(12) United States Patent
Schütz

(10) Patent No.: US 6,829,801 B2
(45) Date of Patent: Dec. 14, 2004

(54) ELECTRONIC TOOTHBRUSH

(75) Inventor: Alfred Schütz, Zollikofen (CH)

(73) Assignee: Gimelli Produktions AG, Zollikofen (CH)

( * ) Notice: Subject to any disclaimer, the term of this patent is extended or adjusted under 35 U.S.C. 154(b) by 181 days.

(21) Appl. No.: 09/977,576

(22) Filed: Oct. 16, 2001

(65) Prior Publication Data

US 2002/0066147 A1 Jun. 6, 2002

(30) Foreign Application Priority Data

Oct. 16, 2000 (DE) .......................................... 100 51 256
Feb. 12, 2001 (DE) .......................................... 101 06 665
Feb. 21, 2001 (DE) .......................................... 101 08 373

(51) Int. Cl.[7] .............................................. A61C 17/34
(52) U.S. Cl. .......................................... 15/28; 15/22.1
(58) Field of Search ..................................... 15/22.1, 28

(56) References Cited

U.S. PATENT DOCUMENTS

| 1,255,028 | A | * | 1/1918 | Leonard et al. ............... 601/89 |
| 4,479,516 | A | * | 10/1984 | Hunter ........................ 15/22.1 |
| 5,416,942 | A | * | 5/1995 | Baldacci et al. ............. 15/22.1 |
| 5,617,603 | A | | 4/1997 | Mei ............................. 15/22.1 |
| 5,732,432 | A | * | 3/1998 | Hui ............................. 15/22.1 |
| 5,784,743 | A | * | 7/1998 | Shek ........................... 15/22.1 |

FOREIGN PATENT DOCUMENTS

| DE | 29914615 | 1/2000 |
| DE | 19927297 | 6/2000 |

* cited by examiner

*Primary Examiner*—Mark Spisich
(74) *Attorney, Agent, or Firm*—Crowell & Moring LLP

(57) ABSTRACT

An electric toothbrush having a cam disc mounted at the free end of a toothbrush shaft and which engages between two follower pins of a bristle carrier disc. The form of the cam disc is approximately elliptical. This causes it to impart a reciprocating motion to the bristle carrier disc when the toothbrush shaft is driven in rotation.

16 Claims, 7 Drawing Sheets

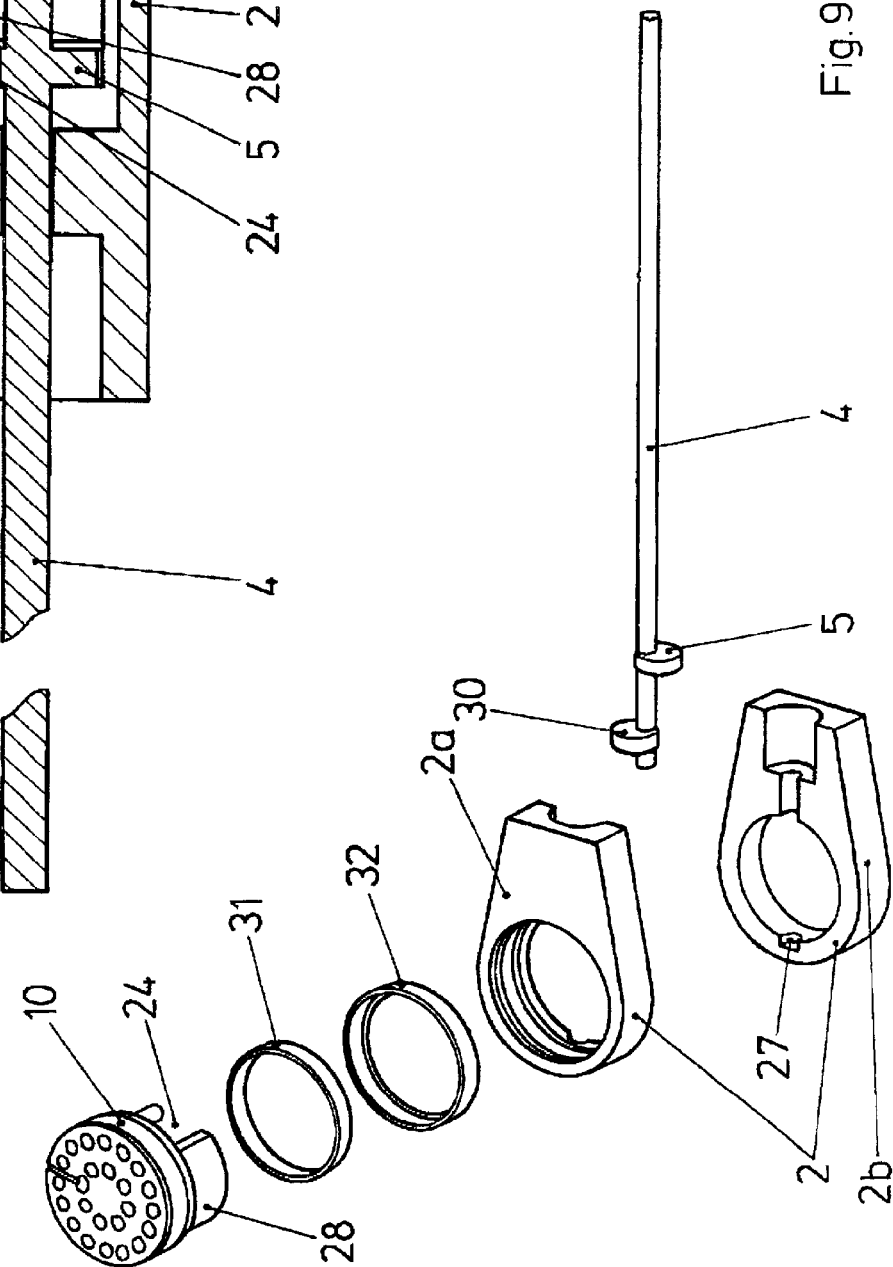

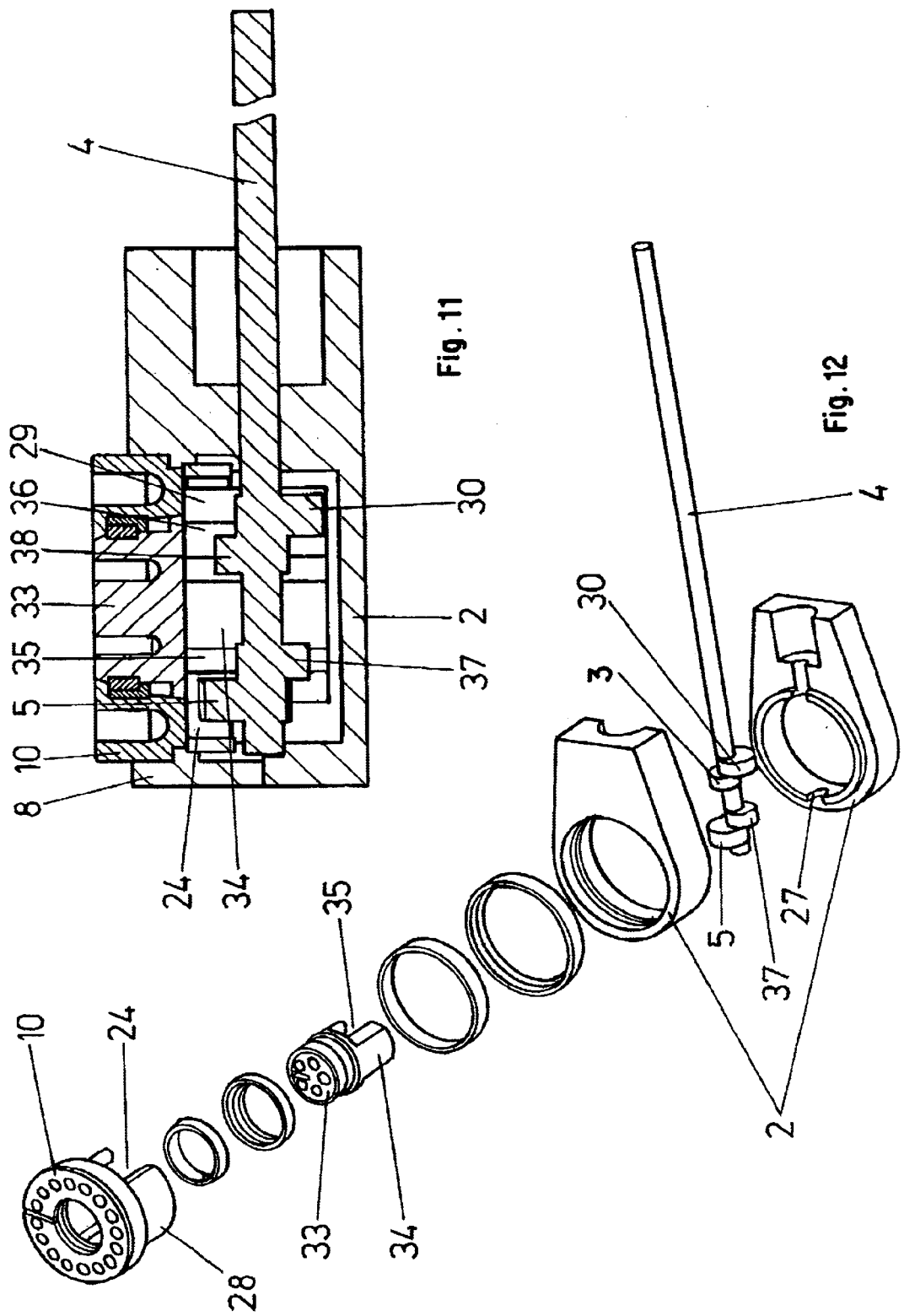

ELECTRONIC TOOTHBRUSH

BACKGROUND AND SUMMARY OF THE INVENTION

This application claims the priority of German application No 101 08 373.4, filed Feb. 21, 2001, the disclosure of which is expressly incorporated by reference herein.

This invention relates to an electric toothbrush and, more particularly, this invention relates to an electric toothbrush with a toothbrush shaft rotating in a brush casing and a bristle carrier disc which are connected to each other by a gear that converts the one-way rotary motion of the toothbrush shaft into a reciprocating rotary motion of the bristle carrier disc, and wherein the toothbrush shaft has at its end lying towards the rotatably mounted bristle carrier disc an eccentric which engages in a gap in the bristle carrier disc bounded by two bearing surfaces.

Such a toothbrush is known from WO 96/37164. The gap is formed by a slot in the bristle carrier disc, and the eccentric is formed by a double crank at the end of the toothbrush shaft. The free end of the crank must be aligned with the center of the bristle carrier disc in order for the eccentric to operate without play in the slot in all angular positions. To obtain adequate resistance to wear and the requisite absence of play and at the same time low friction in the known toothbrush, it is necessary that the toothbrush shaft be formed as a metal part, which greatly increases the cost of manufacture of the electric toothbrush.

The fundamental problem of the invention is to design an electric toothbrush of the kind stated at the outset so that all, or as nearly as possible all, of its parts can be produced as injection molded parts.

In accordance with the invention this problem is solved by forming the eccentric as a cam disc which is arranged on the toothbrush shaft and bridges the gap in every angular position.

This configuration enables the toothbrush shaft and cam disc to be formed as simple injection molded parts, or even to be combined as one injection molding. It means that sufficient absence of play can be achieved with standard manufacturing accuracies as the cam disc (disregarding its necessary eccentricity) does not need to be aligned with the center of the bristle carrier disc. Furthermore, if the toothbrush shaft and the cam disc are made as two parts, different angles of sweep of the bristle carrier disc can be obtained by fitting different cam discs.

In one embodiment that is especially advantageous, the cam disc has a surrounding helical groove which extends obliquely with respect to the cam disc, and the groove bottom forms the eccentric and bridges the gap between the two follower pins. This configuration results in, not point contact but line contact between the follower pins and the cam disc, and hence in a considerable reduction in wear.

In the embodiments which have so far been described, a cam disc engages in a slot in the bristle carrier disc on one side of the axis of rotation of the bristle carrier disc. A symmetrical and therefore torsionless application of force can be obtained if the bristle carrier disc has gaps disposed symmetrically and diametrically with respect to its axis of rotation and the toothbrush shaft accordingly has two cam discs oriented in opposite directions and each engaging in one of the gaps. The result is a quieter oscillating action of the bristle carrier disc. Furthermore, axially directed forces on the toothbrush shaft are avoided.

In one particularly simple construction of the electric toothbrush, the bristle carrier disc is rotatably seated in the barrel by its lateral cylindrical face and the toothbrush shaft passes underneath the bristle carrier disc to a bearing in the brush head on the same side as the free end of the brush casing. Such an embodiment can be manufactured at much lower cost than the embodiments which have so far been described.

The invention also makes it possible to impart different motions to different sets of bristles in the brush part, by rotatably mounting, concentrically within the bristle carrier disc, a further bristle carrier disc which likewise has an extension with opposing gaps in each of which, in a similar fashion to the cam discs for the outer bristle carrier disc, a cam disc of the toothbrush shaft engages, so that the toothbrush shaft has four cam discs altogether.

In a particularly simple embodiment, the two bearing surfaces extend parallel with each other and bear against the eccentric, and the eccentric is formed as a non-circular, approximately elliptical cam disc. The effect of this configuration is to compensate for the variation in the distance between the two bearing surfaces (viewed in projection) in the course of the reciprocating motion.

The toothbrush will operate with particularly low levels of play and friction if the bearing surfaces present a convex curvature to the lateral face of the eccentric. This ensures that the bearing surface extends tangentially to the lateral face of the cam disc at all times.

In a further configuration of the inventive toothbrush, the two bearing surfaces extend parallel with each other and bear against the eccentric and in the eccentric is formed as a non-circular, approximately elliptical cam disc.

In another embodiment, the bearing surfaces present a convex curvature to the lateral face of the cam disc.

In still another embodiment, the gap is formed between two follower pins projecting from a lower end face of the bristle carrier disc and the bearing surfaces are provided on these follower pins.

In yet another embodiment, close to its cam disc the toothbrush shaft has a rotating collar which fits into a bearing shell in the brush casing.

In a further embodiment, a section of the brush casing is formed by a lid which is removably inserted in an opening in the brush casing and forms part of the bearing shell.

In another configuration of the inventive toothbrush, the lid also forms a section of a holder for the bristle carrier disc.

Other objects, advantages and novel features of the present invention will become apparent from the following detailed description of the invention when considered in conjunction with the accompanying drawings.

BRIEF DESCRIPTION OF THE DRAWINGS

FIG. 8 is a longitudinal cross-section through the region of the brush head of a further embodiment of the invention;

FIG. 9 is a perspective exploded view showing the arrangement of FIG. 8;

FIG. 10 is a perspective view of the bristle carrier disc according to FIGS. 8 and 9;

FIG. 11 is a longitudinal cross-section through the region of the brush head of a further embodiment of the invention; and FIG. 12 is a perspective exploded view showing the arrangement of FIG. 11.

DETAILED DESCRIPTION OF THE PREFERRED EMBODIMENTS

Figure 1:
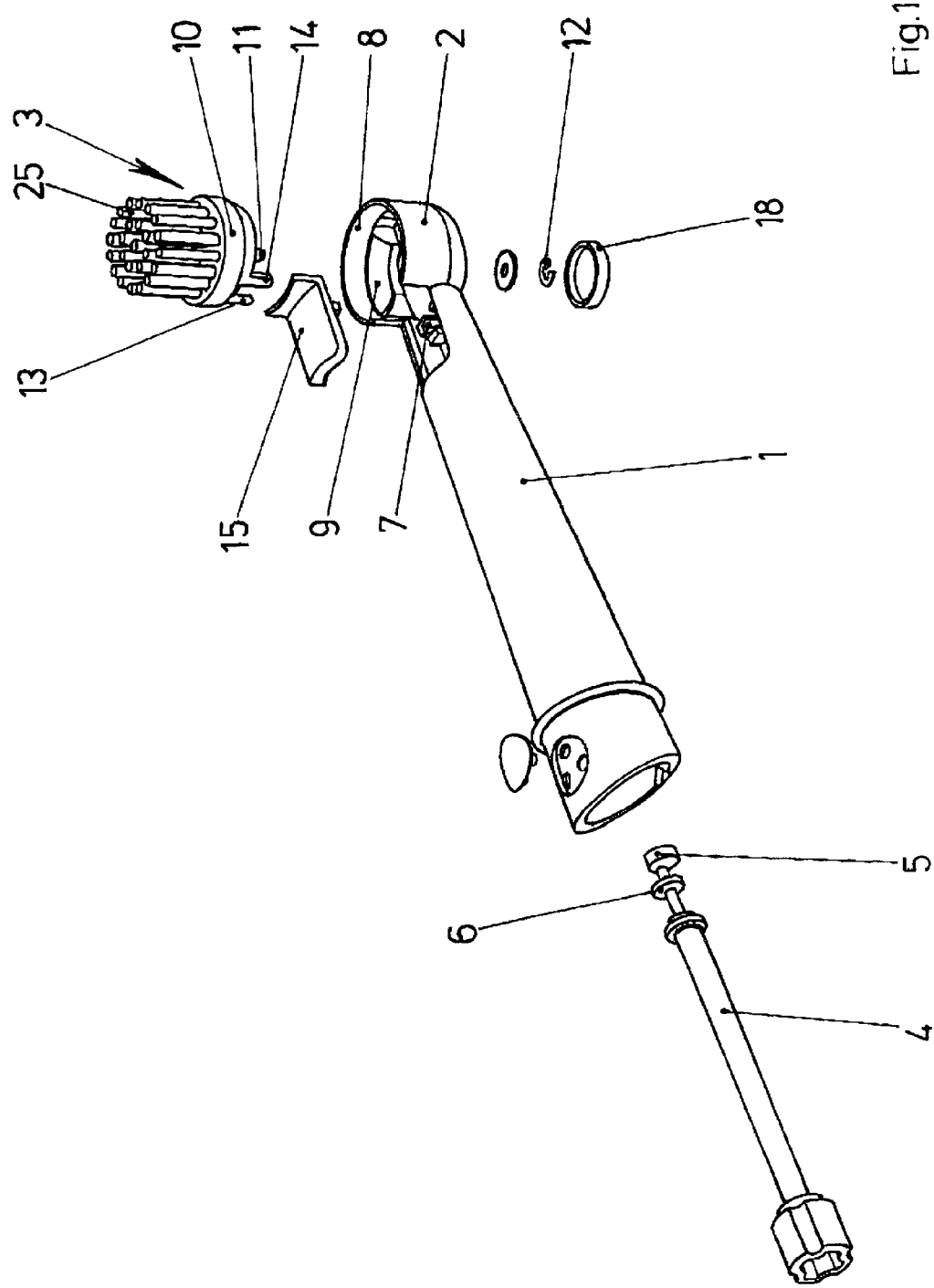
FIG. 1 is an exploded view of a casing and head of a toothbrush.

FIG. 1 shows a brush casing 1 of a clip-on brush of an electric toothbrush. The brush casing 1 is formed as an elongated hollow cylinder which is connectable at one end to a handpiece of the electric toothbrush (not shown) and merges at the other end into a bowl-shaped brush head 2 for a brush part 3. Mounted inside the brush casing 1 is a toothbrush shaft 4 which can be coupled at one end with a motor in the handpiece of the toothbrush, and carries at its other end an eccentric cam disc 5 whose precise shape will be described in detail presently. Located behind the cam disc 5 on the toothbrush shaft 4 is a bearing collar 6 which is held in a bearing shell 7 of the brush casing 1.

The brush head 2 has a barrel 8 which is open at the top and is partly closed underneath by a bottom 9. The brush part 3 has bristles 25 set in a bristle carrier disc 10. When fitted, the bristle carrier disc 10 is rotatably held in the barrel 8. A journal 11 passes through the bottom 9, and is retained externally by a circlip 12.

Two follower pins 13, 14 project downwards from the bristle carrier disc 10. They extend parallel with but at a certain distance from the journal 11. A sector of the bottom 9 corresponding to the angle of sweep of the bristle carrier disc 10 is relieved.

A portion of the barrel 8 and of the brush casing 1 is cut away, and is closed by a lid 15 completely covering the cutaway areas; the significance of this lid 15 will become apparent in particular from the description of FIG. 2 which will now be given.

Figure 2:
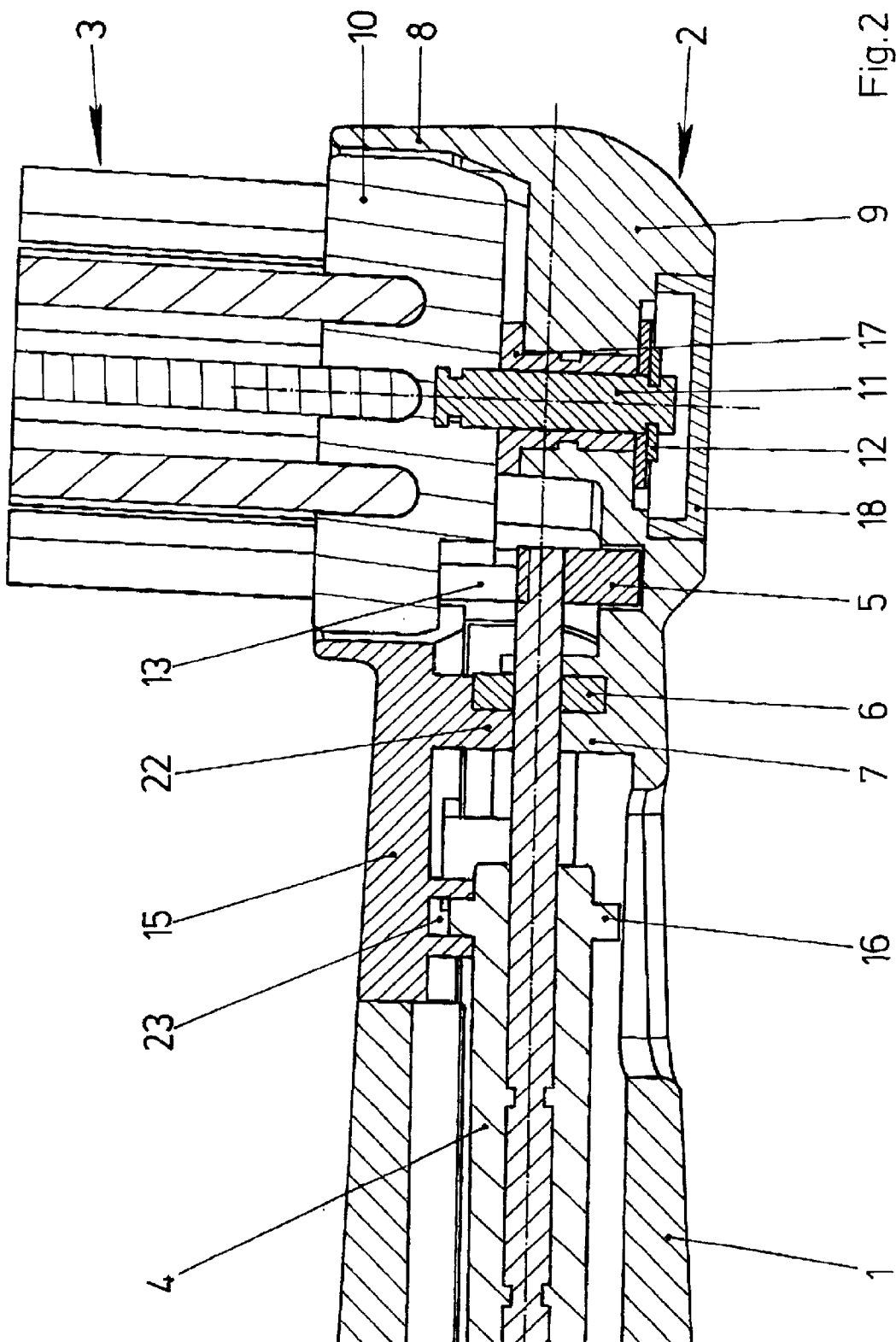
FIG. 2 is a side elevational view in cross-section showing the components of FIG. 1.

FIG. 2 shows a forward region of the assembled clip-on brush viewed in longitudinal section. The toothbrush shaft 4 is inserted into the brush casing 1 from the "plug-in" end. As the lid 15 has not yet been closed, the bearing collar 6 located just behind the cam disc 5 can be placed in the bearing shell 7. The lid 15 has a shoulder 22 which fits over the toothbrush shaft 4 above the bearing shell 7 thereby fixing the shaft in the position shown.

Further away from the brush head 2, the toothbrush shaft 4 has a bearing collar 16 over which a slot 23 of the lid 15 fits, thereby additionally fixing the toothbrush shaft 4 in the axial direction. The actual cam disc 5 is inside the brush head 2 for the brush part 3. After assembly of the bristle carrier disc 10, the follower pins 13, 14, of which only the pin 13 can be seen in FIG. 2, fit over the cam disc 5 on opposite sides. The journal 11 passes through a bearing sleeve 17 inserted in the bottom 9 and is retained by a circlip 12, which lies in a recess, closed by a cap 18, on the outside of the bottom 9. Assembly is completed by closing the brush casing 1 by means of the lid 15.

Figure 3:
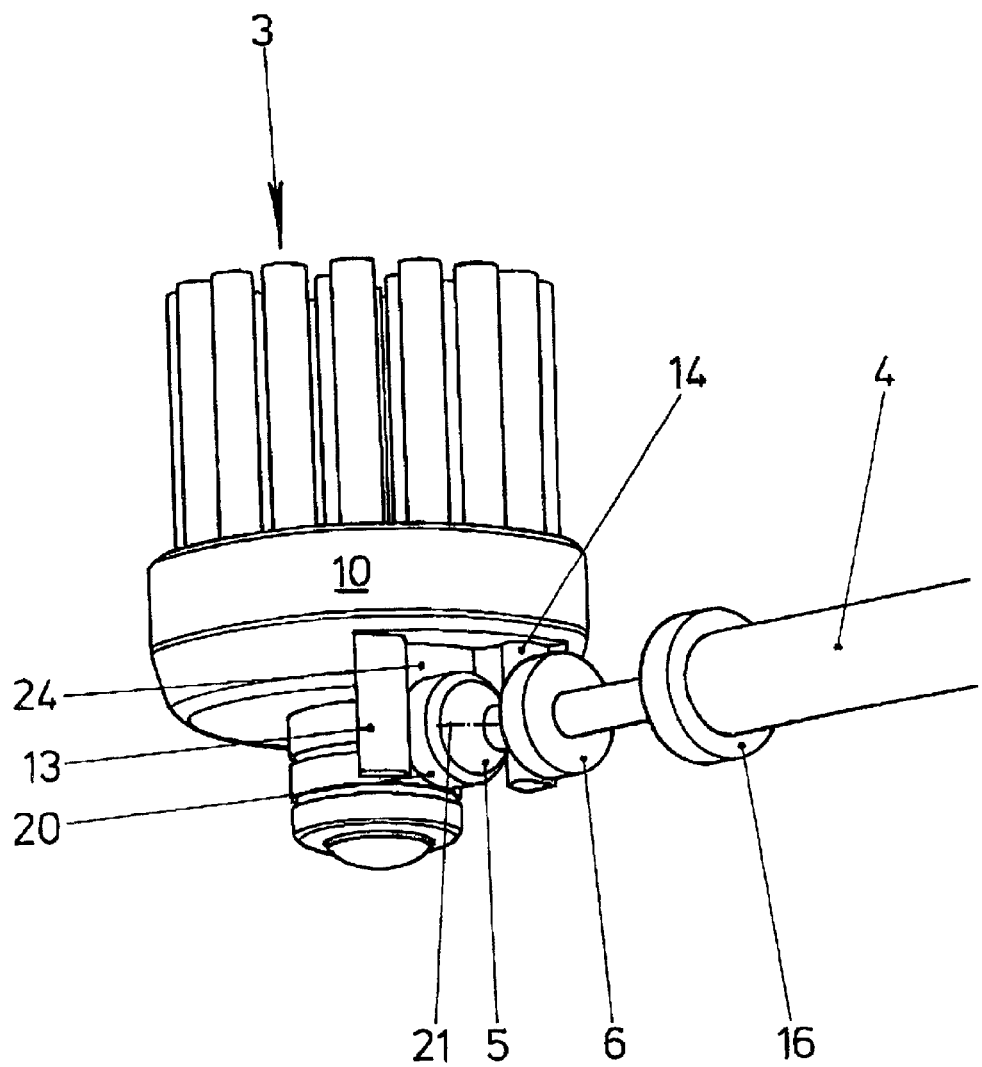
FIG. 3 is a perspective view of the gear between the toothbrush shaft and the brush head.

FIG. 3 shows details of the gear formed from the cam disc 5 at the end of the toothbrush shaft 4 and the two follower pins 13, 14 on the bristle carrier disc 10. It will be seen that the cam disc 5 is attached to be toothbrush shaft 4 with extreme eccentricity; it is this eccentricity which determines the angle of sweep of the bristle carrier disc 10 as it turns to and fro. The crucial feature is that the cam disc 5 bridges the gap between the follower pins 13, 14, substantially without play, at all times, so that there is a smooth and jolt-free transition from one direction of motion to the other.

Because the follower pins 13, 14 move on circular paths about the journal 11, there are some special features that should be noted. First of all, there is a variation in the orientation of the follower pins 13, 14 with respect to the lateral face 20 of the cam disc 5. This is clearly seen by comparing FIGS. 4 and 5; as the follower pins 13, 14 move away from the shaft 4 the angle at which they rest on the lateral face 20 becomes more acute. The sides of the follower pins 13, 14 forming the bearing surfaces are therefore curved, so that the lateral face 20 forms a tangent to the bearing face concerned at all times. Also, they move back and forth with respect to the cam disc 5. For this reason, the cam disc 5 has a certain thickness, and its lateral face 20 therefore has a certain longitudinal extent.

Figure 4:
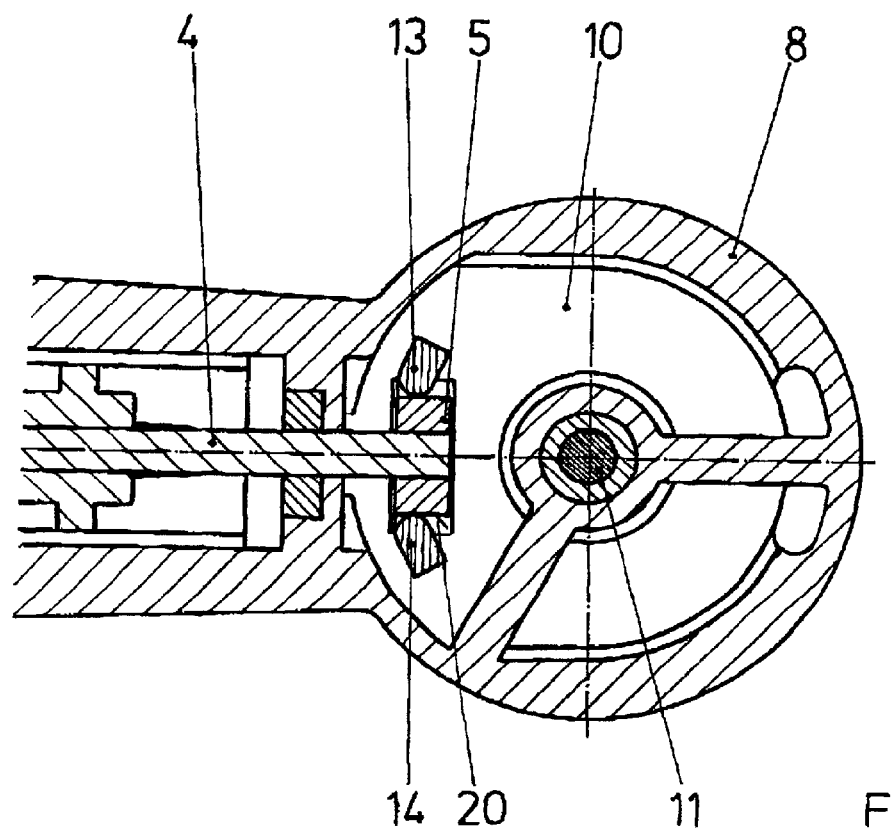
FIG. 4 is a cross-section through the gear with the brush head at the central point of its reciprocating path.

Moreover it should be noted that the gap between the follower pins 13, 14, when viewed in the direction parallel with the toothbrush shaft 4, varies with the angular position of the bristle carrier disc 10. This has implications for the outer contour of the cam disc. FIG. 4 shows the section through the theoretically circular cam disc 5 when its radius of eccentricity 21 (shown in FIG. 3), that is the line joining the center of the disc and the axis of rotation determined by the toothbrush shaft 4, is parallel with the follower pins 13, 14. The projection of the cam disc is equal on either side of the line of the radius of eccentricity 21. Hence the bristle carrier disc 10 is in its central position. The diameter of the cam disc 5 perpendicular to the line of the radius of eccentricity 21 will be referred to as the major diameter.

Figure 5:
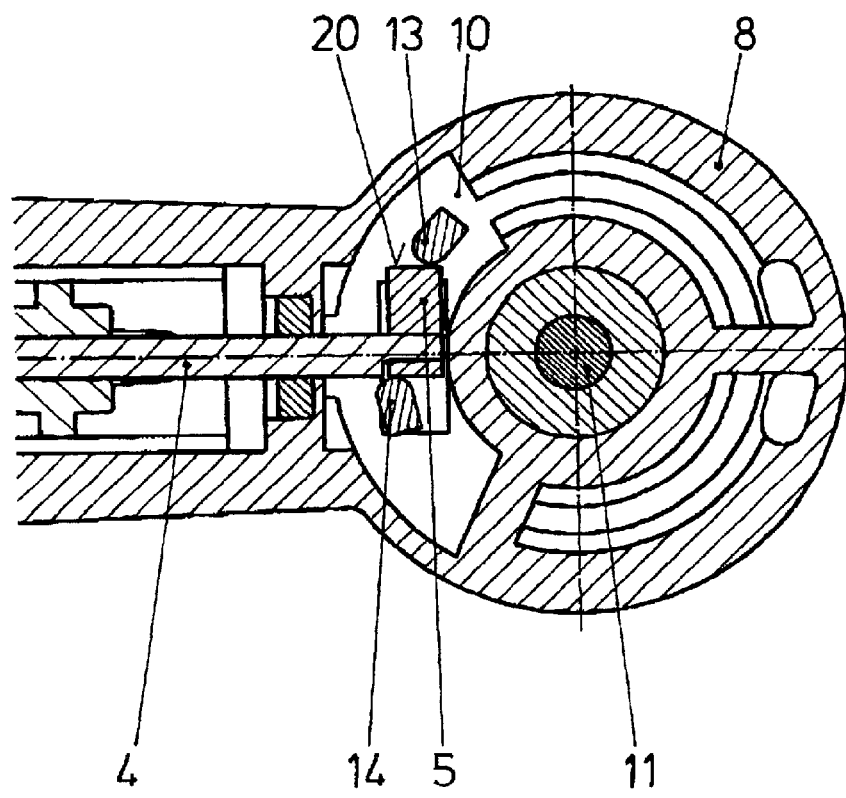
FIG. 5 is a cross-section through the gear with the brush head rotated away from the central point.

After a rotation through 90°, the radius of eccentricity 21 lies perpendicular to the follower pins 13, 14 and the bristle carrier disc 10 has now been rotated to the furthest position from its central position. This situation is shown in FIG. 3 and FIG. 5. The gap between the follower pins 13, 14 has decreased, in the projection plan formed by the cam disc 5. The diameter of the cam disc in this direction must also be decreased. This diameter is therefore smaller on the line of the radius of eccentricity than the major diameter defined above. The transition between the diameters is a continuous one, giving the cam disc an approximately elliptical outer contour.

Figure 6:
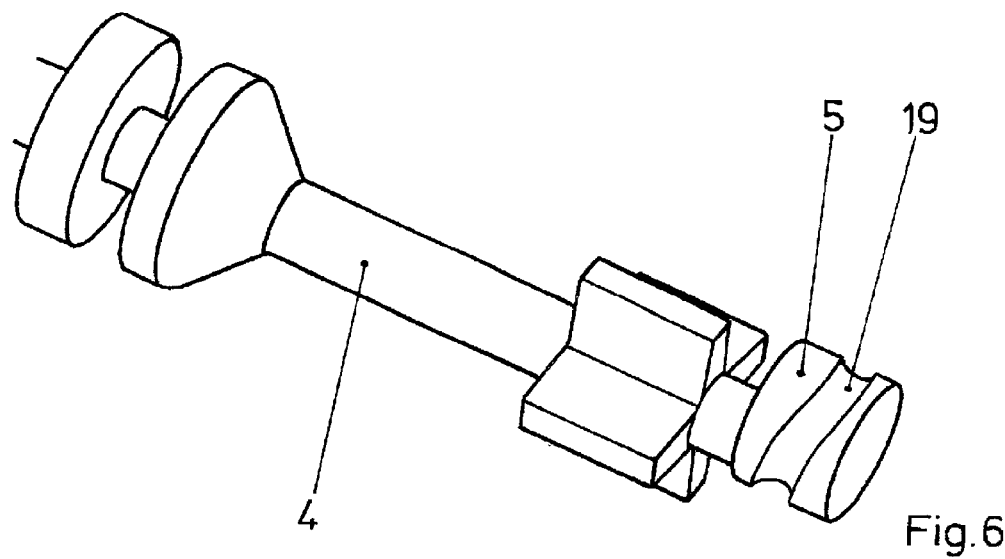
FIG. 6 is a perspective view of a second embodiment of the toothbrush, in the region of the toothbrush shaft.
Figure 7:
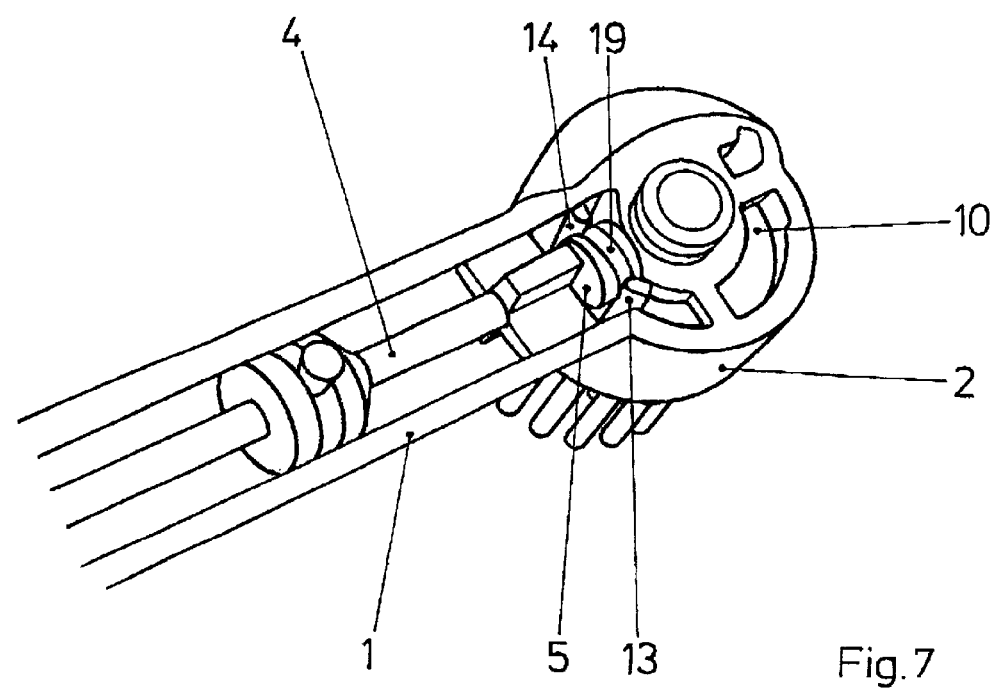
FIG. 7 is a perspective view of the brush casing, with the brush casing partially broken away for illustrative clarity, with components mounted therein in accordance with the second embodiment of the invention.

In the embodiment shown in FIGS. 6 and 7, an oblique surrounding helical groove 19 is provided in the lateral face of the cam disc 5. The bottom of this helical groove 19 forms the eccentric of the cam disc 5 in this embodiment.

FIG. 7 shows that the two follower pins 13, 14 of the bristle carrier disc 10 engage in this helical groove 19. Therefore the rotary motion of the toothbrush shaft 4 again causes a reciprocating motion of the bristle carrier disc 10.

In the embodiment shown in FIG. 8, the bristle carrier disc 10 is rotatably seated by its lateral cylindrical face 26 in the barrel 8 of the brush head 2. The toothbrush shaft 4 passes under the bristle carrier disc 10 to a bearing 27 in the outer side of the brush head. The bristle carrier disc 10 has on the side towards the toothbrush shaft 4 a ring-shaped extension 28 in which a gap 29 is provided, in addition to the gap 24 on the opposite side. The toothbrush shaft 4 engages by a cam disc 5 in the gap 24, just as in the embodiments previously described. However, the toothbrush shaft 4 has a second cam disc 30 to the bearing 27. This second cam disc 30 is oriented the opposite way to the cam disc 5, and engages in the second gap 29

The purpose of the perspective exploded view in FIG. 9 is to further elucidate the construction of the embodiment shown in FIG. 8. The toothbrush shaft 4 is seen, with its two cam discs 30 and 5. Also to be seen in FIG. 9 is the bristle carrier disc 10 with its extension 28 and with the gap 24 in which the cam disc 5 engages. The brush head 2 consists of two shells 2a, 2b. Two rings 31, 32 are inserted in the upper shell 2a. These rings determine the axial position of the bristle carrier disc 10 within the barrel 8 of the brush head 2.

The detail drawing of the bristle carrier disc 10 in FIG. 10 reveals the two opposing gaps 29, 24 in the extension 28 of the bristle carrier disc 10, in which the cam discs 30, 5 respectively engage.

In the embodiment shown in FIG. 11, a further bristle carrier disc 33 is rotatably inserted inside the bristle carrier disc 10. The outer bristle carrier disc 10 is, therefore, ring-shaped. Just like the outer bristle carrier disc 10, the inner bristle carrier disc 33 has an extension 34 with two gaps 35, 36 in each of which a cam disc 37, 38 of the toothbrush shaft 4 engages, producing a reciprocating motion. The toothbrush shaft 4 in this embodiment therefore has a total of four cam discs 5, 37, 38, 30.

The perspective exploded view in FIG. 12 shows the ring-shaped bristle carrier disc 10 with its extension 28 and a gap 24. Also visible is the bristle carrier disc 33 with its extension 34 and a gap 35. The toothbrush shaft 4 of FIG. 12 is shown in the same way as that of FIG. 9 but now has four cam discs 5, 37, 38, 30. Also to be seen in FIG. 12 is one half of the bearing 27 in which the free end of the toothbrush shaft 4 is mounted in the brush head 2.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An electric toothbrush comprising a brush casing, a toothbrush shaft adapted to rotate in said brush casing, and a bristle carrier disc which is connected to one end of said toothbrush shaft by a gear arrangement that converts one-way rotary motion of the toothbrush shaft into a reciprocating rotary motion of the bristle carrier disc; said bristle carrier disc comprising a pair of bearing surfaces and at least one gap therebetween; said gear arrangement comprising an eccentric mounted at said one end of said toothbrush shaft, said eccentric engaging in said gap in the bristle carrier disc, and wherein the eccentric is formed by at least one cam disc which bridges the gap in every angular position, wherein the two bearing surfaces extend parallel with each other and bear against the eccentric and the eccentric is formed as a non-circular, approximately elliptical cam disc.

2. An electric toothbrush according to claim 1, further comprising a rotating collar mounted on the toothbrush shaft in the vicinity of the cam disc, said collar fitting into a bearing shell in the brush casing.

3. An electric toothbrush according to claim 2, wherein a section of the brush casing is formed by a lid which is removably inserted in an opening in the brush casing and which forms part of the bearing shell.

4. An electric toothbrush according to claim 3, wherein the lid also forms a section of a holder for the bristle carrier disc.

5. An electric toothbrush according to claim 1, wherein the bristle carrier disc has two gaps disposed symmetrically and diametrically with respect to its axis of rotation and the toothbrush shaft accordingly has two cam discs oriented in opposite directions and each engaging in one of the gaps.

6. An electric toothbrush according to claim 5, wherein said casing comprises a barrel at one end thereof and the bristle carrier disc rotatably seated in the barrel by its lateral cylindrical face and the toothbrush shaft passes underneath the bristle carrier disc to a bearing in the brush head on the same side as the free end of the brush casing.

7. An electric toothbrush according to claim 5, further comprising a further bristle carrier disc rotatably mounted concentrically inside the bristle carrier disc, said further bristle carrier disc comprising an extension with two opposing gaps, and a pair of cam discs mounted on said toothbrush shaft, each of said pair of cam discs engages one of said opposing gaps.

8. An electric toothbrush comprising a brush casing, a toothbrush shaft adapted to rotate in said brush casing, and a bristle carrier disc which is connected to one end of said toothbrush shaft by a gear arrangement that converts one-way rotary motion of the toothbrush shaft into a reciprocating rotary motion of the bristle carrier disc; said bristle carrier disc comprising a pair of bearing surfaces and at least one an therebetween; said gear arrangement comprising an eccentric mounted at said one end of said toothbrush shaft, said eccentric engaging in said gap in the bristle carrier disc, and wherein the eccentric is formed by at least one cam disc which bridges the gap in every angular position wherein the cam disc comprises a lateral face and the bearing surfaces present a convex curvature to the lateral face of the cam disc.

9. An electric toothbrush according to claim 8, further comprising a rotating collar mounted on the toothbrush shaft in the vicinity of the cam disc, said collar fitting into a bearing shell in the brush casing.

10. An electric toothbrush according to claim 9, wherein a section of the brush casing is formed by a lid which is removably inserted in an opening in the brush casing and which forms part of the bearing shell.

11. An electric toothbrush according to claim 10 wherein the lid also forms a section of a holder for the bristle carrier disc.

12. An electric toothbrush comprising a brush casing, a toothbrush shaft adapted to rotate in said brush casing, and a bristle carrier disc which is connected to one end of said toothbrush shaft by a gear arrangement that converts one-way rotary motion of the toothbrush shaft into a reciprocating rotary motion of the bristle carrier disc; said bristle carrier disc comprising a pair of bearing surfaces and at least one gap therebetween; said gear arrangement comprising an eccentric mounted at said one end of said toothbrush shaft, said eccentric engaging in said gap in the bristle carrier disc, and wherein the eccentric is formed by at least one cam disc which bridges the gap in every angular position wherein the gap is formed between two follower pins projecting from a lower end face of the bristle carrier disc and the follower pins comprise the bearing surfaces.

13. An electric toothbrush according to at claim 12, wherein the cam disc has a surrounding helical groove extending obliquely with respect to the cam disc, with a groove bottom which farms the eccentric and bridges the gap between the two follower pins.

14. An electric toothbrush according to claim 12, further comprising a rotating collar mounted on the toothbrush shaft in the vicinity of the cam disc, said collar fitting into a bearing shell in the brush casing.

15. An electric toothbrush according to claim 14, wherein a section of the brush casing is formed by a lid which is removably inserted in an opening in the brush casing and which forms part of the bearing shell.

16. An electric toothbrush according to claim 15 wherein the lid also forms a section of a holder for the bristle carrier disc.

* * * * *